United States Patent [19]
Markovs et al.

[11] Patent Number: 5,089,034
[45] Date of Patent: Feb. 18, 1992

[54] PROCESS FOR PURIFYING NATURAL GAS

[75] Inventors: John Markovs, Yorktown Heights, N.Y.; Frederick E. James, Jr., Stamford, Conn.

[73] Assignee: UOP, Des Plaines, Ill.

[21] Appl. No.: 612,934

[22] Filed: Nov. 13, 1990

[51] Int. Cl.$^5$ .............................................. B01D 53/04
[52] U.S. Cl. ........................................... 55/28; 55/31; 55/33; 55/62; 55/66; 55/68; 55/74; 55/75
[58] Field of Search ................... 55/28, 31, 33, 59, 62, 55/66, 68, 74, 75

[56] References Cited

U.S. PATENT DOCUMENTS

| | | | |
|---|---|---|---|
| 3,150,942 | 9/1964 | Vasan | 55/31 |
| 3,359,707 | 12/1967 | Jean | 55/33 |
| 3,594,983 | 7/1971 | Yearout | 55/33 |
| 3,594,984 | 7/1971 | Toyama et al. | 55/33 |
| 3,738,084 | 6/1973 | Simonet et al. | 55/31 |
| 3,841,058 | 10/1974 | Templeman | 55/33 |
| 4,025,321 | 5/1977 | Anderson et al. | 55/33 |
| 4,233,038 | 11/1980 | Tao | 55/33 |
| 4,249,915 | 2/1981 | Sircar et al. | 55/33 X |
| 4,472,178 | 9/1984 | Kumar et al. | 55/28 X |
| 4,504,295 | 3/1985 | Davis et al. | 62/30 |
| 4,662,919 | 5/1987 | Davis | 62/25 |
| 4,702,898 | 10/1987 | Grover | 423/220 |
| 4,711,645 | 12/1987 | Kumar | 55/31 X |
| 4,784,672 | 11/1988 | Sircar | 55/28 X |
| 4,986,835 | 1/1991 | Uno et al. | 55/31 X |

FOREIGN PATENT DOCUMENTS

| | | | |
|---|---|---|---|
| 972284 | 10/1964 | United Kingdom | 55/31 |
| 2055609 | 3/1981 | United Kingdom | 55/31 |
| 2181667 | 4/1987 | United Kingdom | |

OTHER PUBLICATIONS

Lugosch, Economies of Scale in Small Nitrogen Rejection Units, Proceedings of the Sixty-Fifth Annual Convention, Gas Processors Association, 1986, pp. 96–104.

*Primary Examiner*—Robert H. Spitzer
*Attorney, Agent, or Firm*—Thomas K. McBride; John G. Tolomei; Warren K. Volles

[57] ABSTRACT

Processes are disclosed for separating water and carbon dioxide from hydrocarbon streams, e.g., natural gas, by adsorption prior to low temperature hydrocarbon processing operations, e.g., liquid natural gas recovery and nitrogen rejection. The processes employ separate adsorption zones for the water and carbon dioxide adsorption and both adsorption zones are operated with a thermal swing adsorption cycle. A product gas from the low temperature processing operation, e.g., methane, can be used as the purge gas for one or both adsorption zones and the desorbed water and carbon dioxide, along with the purge gas can be recovered and introduced into a natural gas pipeline, for example.

26 Claims, 1 Drawing Sheet

Figure 1

PROCESS FOR PURIFYING NATURAL GAS

FIELD OF THE INVENTION

The present invention is generally related to processes for purifying hydrocarbons. More specifically, the present invention is directed to improved processes for removing water and carbon dioxide from hydrocarbon feedstreams, such as natural gas, prior to low temperature processing of the hydrocarbon feedstream.

BACKGROUND OF THE INVENTION

In the low temperature processing of hydrocarbon feedstreams, e.g., liquefaction of natural gas, it is often necessary to reduce the concentration of water and carbon dioxide in the feedstream prior to any low temperature processing in order to prevent solidification of those components, commonly known as freeze-up. Some typical low temperature processing operations wherein such purification is required include nitrogen rejection, helium recovery, liquified natural gas processing operations and deep ethane recovery.

It is common practice in processes such as disclosed above to utilize molecular sieve dehydration to meet the low dew point requirements in the low temperature gas processing facilities which recover hydrocarbons. It is also common practice to employ liquid absorption processes such as those using solvents containing alkanol amines to remove carbon dioxide from the feedstreams. For example, U.S. Pat. No. 4,702,898, issued to Grover discloses a process for the removal of acid gases from mixtures which utilizes an alkaline scrubbing solution to remove the acid gases, e.g., carbon dioxide, from the gas mixtures. In addition to acid gas absorption, solid absorbents, e.g., molecular sieves, can be employed for the further removal of carbon dioxide depending upon the ability of the liquid absorption system to remove carbon dioxide and upper limits on the permissible carbon dioxide concentration. For example, adsorption is often employed when it is necessary to substantially remove carbon dioxide to levels of about 50 to 200 ppmv carbon dioxide, such as is typically required in liquefaction or deep ethane recovery. In some instances, it can be desirable to eliminate the liquid carbon dioxide absorption unit and perform the carbon dioxide removal by molecular sieve adsorption along, e.g., for purification where bulk carbon dioxide removal is not required.

In typical low temperature hydrocarbon processing operations where adsorbents are used to remove water and carbon dioxide, both components are removed in the same adsorber bed. Note, for example, U.K. Patent Application GB 2 181 667A published Apr. 29, 1987 which discloses a process wherein both carbon dioxide and water vapor are removed from a natural gas feed in an adsorber bed. However, adsorption systems which are designed to remove both water and carbon dioxide in a single adsorber bed can be plagued with major problems. For instance, it is known that water is a strongly adsorbed component whereas carbon dioxide is much less strongly adsorbed. Hence, since adsorption is favored at lower temperatures, it is typically desirable to perform the carbon dioxide adsorption at the lowest temperatures possible. However, the temperatures are limited by the formation of hydrates in the presence of water at low temperatures which can cause plugging or blockage problems. Hydrates can be defined as solid materials formed by the combination of a hydrocarbon with water, usually at low temperatures. Similarly, because water is more strongly adsorbed than carbon dioxide, it is usually desirable to regenerate the water-loaded adsorbent at a substantially higher temperature than is necessary to regenerate the carbon dioxide-loaded adsorbent. Moreover, at typical regeneration temperatures for regenerating water-loaded adsorbent beds, e.g., above 500° F., the hydrocarbons present in the adsorber bed can be converted to carbon oxides and water when there is oxygen present in the regeneration gas. Thus, there can be a built-up of carbon oxides and water in the system. This type of problem is addressed in U.S. Pat. No. 4,025,321, issued to Anderson et al.

An adsorption system having separate dehydration and carbon dioxide adsorber beds has been proposed. U.S. Pat. No. 3,841,058, issued to Templeman, discloses a method of purifying natural gas or the like to render it suitable for liquefaction. The method consists essentially of adsorbing water and methanol from a stream of natural gas containing water, methanol and carbon dioxide in a first bed of an adsorbent material and subsequently adsorbing the carbon dioxide in a second bed of adsorbent material. The first adsorber bed is regenerated by passing a gas therethrough at an elevated temperature, i.e., thermal swing adsorption. The second adsorber bed is regenerated by reducing the pressure within the bed and also by passing a gas therethrough at a low temperature to displace desorbed carbon dioxide from the adsorber bed, i.e., a pressure swing adsorption cycle. The patent discloses that the adsorption effluent gas from the first adsorber bed can be cooled to subambient temperatures to increase the adsorptive capacity of the molecular sieves for carbon dioxide.

The method disclosed in above-identified U.S. Pat. No. 3,841,058, however, does not provide an adequate solution to the problem of removing water and carbon dioxide prior to low temperature processing. More specifically, because the second adsorber bed is regenerated by pressure swing adsorption, there is inherently less hydrocarbon recovery due to the fact that pressure swing cycles are usually operated at a shorter cycle time than thermal swing cycles, e.g., minutes versus hours, and hence, the hydrocarbon feed gas which remains in the void space after the adsorption step is terminated is lost in the desorption effluent stream when the adsorber bed is depressurized. In addition, because thermal swing adsorption cycles typically provide more complete regeneration than is generally possible with pressure swing cycles, higher residual carbon dioxide levels are present on the adsorbent subjected to pressure swing regeneration. The higher residual levels cause higher levels of carbon dioxide in the product gas since the concentration of carbon dioxide in the product gas is in equilibrium with the carbon dioxide adsorbed on the adsorbent in the effluent end of the adsorber bed. In order to keep the carbon dioxide content of the adsorbent low in the effluent end of the adsorber bed it is necessary to reduce the cycle time, however, reduced cycle times contribute to the recovery losses described above. Hence, the above-identified patent describes a process that is deficient due to the use of the pressure swing adsorption cycle in the second adsorber bed as compared to a thermal swing cycle.

As noted above, nitrogen rejection operations are one of the low temperature processes which often require the removal of water and carbon dioxide from the hydrocarbon feedstream before it can be further processed. Hydrocarbon fractions obtained from oil and gas wells often contain nitrogen which can be present naturally or as a result of petroleum production methods which frequently utilize high pressure nitrogen injection to maintain well head pressure for enhanced oil and gas recovery. In enhanced recovery operations as nitrogen is injected, the natural gas from the well containing methane and associated hydrocarbon liquids also contains nitrogen which typically increases in amount over the life of the nitrogen injection project to levels above pipeline specifications. Also, it is not uncommon for naturally occurring nitrogen levels to be above pipeline specifications. For these reasons, natural gas which contains nitrogen must be separated to reject the nitrogen and form purified natural gas feedstreams suitable for utilization as fuel or chemical feedstreams. It can also be desirable to reject nitrogen to avoid pricing penalties applied to nitrogen-containing natural gas feedstreams.

In nitrogen rejection units, low temperature distillation is typically employed to separate the nitrogen fraction from the natural gas. Both single and multi-column arrangements have been proposed to accommodate varying nitrogen contents in the raw natural gas. For example, U.S. Pat. No. 4,504,295, issued to Davis et al., discloses a process for the recovery of methane, nitrogen and natural gas liquids from a natural gas feedstream which utilizes a nitrogen rejection stage including a heat pump driven distillation column and a natural gas liquid stage. This patent, for example, discloses at column 5, lines 29-31, that the natural gas feedstream is subjected to bulk carbon dioxide removal and drying. U.S. Pat. No. 4,662,919, issued to Davis, discloses a process for separating or rejecting nitrogen from a natural gas feedstream using a single distillation column. In addition to the above-identified patents, various aspects of nitrogen rejection processing operations including the dehydration and carbon dioxide removal stages are disclosed in the following publication. Lugosch, *Economies of Scale in Small Nitrogen Rejection Units*, Proceedings of the Sixty-Fifth Annual Convention, Gas Processors Association, 1986, at pages 96-104.

Helium recovery is also becoming an important low temperature process because helium is considered to be a valuable commodity. Helium can be recovered in a similar fashion to the rejection processes described above. As with nitrogen rejection processes, it is often necessary in helium recovery operations to remove carbon dioxide and water from the feedstreams to low levels.

Since water and carbon dioxide removal are important and necessary aspects of low temperature hydrocarbon processing operations such as for nitrogen rejection, improved processes are sought which can utilize adsorption technology for both water and carbon dioxide removal. Moreover, processes are sought which can provide improved recovery of the hydrocarbons in the feedstream and also provide desorption effluent streams, i.e., containing water and carbon dioxide, that can be conveniently passed to a pressurized pipeline downstream of the low temperature processing operation without the need for excessive compression.

SUMMARY OF THE INVENTION

By the present invention, processes are provided for separating water and carbon dioxide from hydrocarbon feedstreams. In accordance with the present invention, water and carbon dioxide are removed in separate adsorption zones rather than in a single adsorption zone. As a result, energy savings and improved performance can be achieved. More specifically, the hydrocarbon feedstream, e.g., natural gas, containing carbon dioxide and water is passed to a first adsorption zone wherein the water is adsorbed to provide a dried feedstream which is passed to the second adsorption zone to remove carbon dioxide. Since water is removed in the first adsorption zone, the second adsorption zone can be maintained at a lower temperature than would otherwise be possible if the water had not been removed due to hydrate formation at the lower temperature. Hence, at the lower temperature, more carbon dioxide can removed for a given quantity of adsorbent than at a higher temperature. In addition, because the adsorption zones are separate, the temperatures used for regeneration can likewise be different. That is, the second adsorption zone which contains adsorbed carbon dioxide can be adequately regenerated at moderate regeneration temperatures whereas the first adsorption zone which contains adsorbed water can be regenerated at more typical higher regeneration temperatures. Hence, both the water adsorption capacity and the carbon dioxide adsorption capacity can be enhanced by virtue of the present invention.

Furthermore, in accordance with the present invention the carbon dioxide adsorption zone is regenerated by thermal swing adsorption rather than pressure swing adsorption, which can provide enhanced hydrocarbon recovery. In addition, the present invention makes it possible to use the desorption effluent, i.e., purge gas effluent, from the carbon dioxide adsorption zone to regenerate the water adsorption zone. Thus, Applicants have found that a single purge gas stream can be used for both adsorption zones, thus obviating the need for two separate purge gas streams. Moreover, because the carbon dioxide adsorption zone does not have to be regenerated at an elevated temperature suitable for regenerating the water loaded adsorption zone, it is possible to regenerate the carbon dioxide loaded adsorption zone at a temperature low enough to avoid the conversion of hydrocarbons to carbon oxides and water in the presence of oxygen.

In one aspect of the present invention, there is provided a process for separating water and carbon dioxide from a feedstream comprising hydrocarbons, water and carbon dioxide, the process comprises the steps of: (a) passing the feedstream to a first adsorption zone containing a solid adsorbent having selectivity for water at a first zone adsorption temperature effective to adsorb water and a first zone adsorption pressure and withdrawing a first zone adsorption effluent stream having a reduced concentration of water relative to the feedstream; (b) passing at least a portion of the first zone adsorption effluent stream to a second adsorption zone containing a solid adsorbent having selectivity for carbon dioxide at a second zone adsorption temperature effective to adsorb carbon dioxide and a second zone adsorption pressure, said second zone adsorption temperature being lower than said first zone adsorption temperature, and withdrawing a second zone adsorption effluent stream having a reduced concentration of carbon dioxide relative to the first effluent stream; (c) passing a first purge gas through the first adsorption zone at a first zone regeneration temperature effective to desorb water from the first adsorption zone and a first zone regeneration pressure and withdrawing a first zone desorption effluent stream comprising water; and (d) passing a second purge gas through the second adsorption zone at a second zone regeneration temperature of at least 250° F. and effective to desorb carbon dioxide from the second adsorption zone and a second zone regeneration pressure, said second zone regeneration pressure being not less than 50 psia, and withdrawing a second zone desorption effluent stream comprising carbon dioxide.

In another aspect of the present invention, there is provided a process for separating water and carbon dioxide from a natural gas feedstream comprising water, said carbon dioxide, methane, at least one other hydrocarbon selected from ethane, propane, butanes, pentanes and hexanes, and at least one light gas selected from nitrogen, helium, argon, oxygen and hydrogen. The process comprises the steps of: (a) passing the feedstream to a first adsorption zone containing a solid adsorbent having selectivity for water at a first zone adsorption temperature effective to adsorb water and a first zone adsorption pressure and withdrawing a first zone adsorption effluent stream having a reduced concentration of water relative to the feedstream; (b) passing at least a portion of the first zone adsorption effluent stream to a second adsorption zone containing a solid adsorbent having selectivity for carbon dioxide at a second zone adsorption temperature effective to adsorb carbon dioxide and a second zone adsorption pressure, said second zone adsorption temperature being lower than said first zone adsorption temperature, and withdrawing a second zone adsorption effluent stream having a reduced concentration of carbon dioxide relative to the first effluent stream; (c) separating at least a portion of the second effluent stream into a raw product gas stream rich in methane and a rejection stream comprising said at least one light gas; (d) passing a first purge gas comprising a portion of the raw product gas to the first adsorption zone at a first zone regeneration temperature effective to desorb water from the first adsorption zone and a first zone regeneration pressure and withdrawing a first zone desorption effluent stream comprising water; (e) passing a second purge gas comprising a portion of the raw product gas to the second adsorption zone at a second zone regeneration temperature of at least 250° F. and effective to desorb carbon dioxide from the second adsorption zone and a second zone regeneration pressure, said second zone regeneration pressure being not less than 50 psia, and withdrawing a second zone desorption effluent stream comprising carbon dioxide; and (f) combining the first zone desorption effluent with the remaining portion of the raw product gas to provide a combined product gas rich in methane.

DETAILED DESCRIPTION OF THE INVENTION

The feedstream processed in accordance with the present invention can generally be any hydrocarbon-containing gas which also includes water and carbon dioxide. The origin of the feedstream and its specific chemical make-up, other than as noted herein, are not critical to the present invention. Thus, the feedstream may be a hydrocarbon stream resulting from the destructive hydrogenation of coal or it may be obtained from deposits of natural gas or petroleum. The feedstream is preferably constituted so that it is gaseous at the conditions of the adsorption contacting, described herein. The feedstream preferably includes molecules containing 1 to about 8 carbon atoms. More preferably, the major amount, i.e., about 50% or more, of the hydrocarbon molecules in the feedstream contain 1 to about 4 carbon atoms. A particularly preferred feedstream for treatment in accordance with the present invention is a natural gas that contains at least one of nitrogen, helium, argon, oxygen and hydrogen.

The amount of carbon dioxide in the feedstream is not critical to the present invention. However, from an economic perspective, it is preferred that the carbon dioxide content be such that an economic or processing incentive exists to remove at least a portion of the carbon dioxide from the feedstream. Generally, the carbon dioxide concentration will range from about 200 parts per million by volume (ppmv) to 5 mol. %. More typically, the carbon dioxide content of the feedstream will range from about 500 ppmv to about 3 mol. % by volume of the total feedstream.

The amount of water in the feedstream is also not critical to the present invention but typically ranges from 50 to 7500 ppmv and often up to the saturation limit, particularly when the feedstream is pretreated in an aqueous absorption unit, for example, an amine unit for bulk carbon dioxide removal, hydrogen sulfide removal, or both.

The feedstream may also contain sulfur-containing compounds such as hydrogen sulfide and alkyl mercaptans. When hydrogen sulfide is present in the feedstream, its content is not critical. In fact, the present process is applicable when the feedstream contains small amounts of hydrogen sulfide, e.g., 4 ppmv and when it contains a relatively high concentration of hydrogen sulfide, such as about 300 ppmv or more. Similarly, the alkyl mercaptan content of the feedstream, when present, is not critical. Feedstreams may contain about 20 ppmv and can contain more than about 70 ppmv. The alkyl mercaptans which may be present in the feedstream often include at least one of methyl mercaptan, ethyl mercaptan, propyl mercaptans, butyl mercaptans and mixtures thereof. Although sulfur-containing compounds can be adsorbed in the adsorption zones of the present invention, it is often desirable to pretreat sulfur-containing feedstreams in a liquid absorption unit such as an amine unit.

Examples of gaseous impurities which might be present in trace amounts include sulfur dioxide, carbonyl sulfide and carbon disulfide. Examples of solid or liquid impurities are iron sulfide, iron oxide, high molecular weight hydrocarbons, solvents from absorption units, e.g., glycols and amines, and polymers. Any olefins having more than one double bond, triple bond hydrocarbons and, as a general rule, any material that will polymerize or react in situ is an undesirable impurity.

The feedstream, e.g., natural gas, processed in accordance with the present invention is typically available at a temperature of about 50° to 150° F. and at a pressure of from about 100 to 1700 psia although lower and higher temperatures and pressures are within the scope of the present invention.

The processes of the present invention can be carried out using any suitable adsorbent material or combinations of adsorbent materials having the desired selectivity for water and carbon dioxide. Suitable adsorbents known in the art and commercially available include crystalline molecular sieves, activated carbons, activated clays, silica gels, activated aluminas and the like. Molecular sieves include, for example, the various forms of silicoaluminophosphates, and aluminophosphates disclosed in U.S. Pat. No. 4,440,871; 4,310,440 and 4,567,027, hereby incorporated by reference as well as zeolitic molecular sieves.

Zeolitic molecular sieves in the calcined form may be represented by the general formula;

where Me is a cation, x has a value from about 2 to infinity, n is the cation valence and y has a value of from about 2 to 10.

Typical well-known zeolites which may be used include, chabazite, also referred to as Zeolite D, clinoptilolite, erionite, faujasite, also referred to as Zeolite X and Zeolite Y, ferrierite, mordenite, Zeolite A and Zeolite P. Other zeolites that may be suitable for use according to the present invention are those having a high silica content, i.e., those having silica to alumina ratios greater than 10 and typically greater than 100, although such high silica zeolites are believed to have relatively low capacities for water. One such high silica zeolite is silicalite, as the term used herein includes both the silicapolymorph disclosed in U.S. Pat. No. 4,061,724 and also the F-silicalite disclosed in U.S. Pat. No. 4,073,865, hereby incorporated by reference.

Detailed descriptions of some of the above identified zeolites may be found in D. W. Breck, ZEOLITE MOLECULAR SIEVES, John Wiley and sons, New York, 1974, hereby incorporated by reference. A faujasite-type zeolite ion-exchanged with at least one of zinc, rare earth, hydrogen and ammonium cations useful for separating carbon dioxide from methane is disclosed in U.S. Pat. No. 4,775,396, issued to Rastelli et al., hereby incorporated by reference. A clinoptilolite zeolite suitable for adsorbing carbon dioxide and water from hydrocarbon streams is disclosed in U.S. Pat. No. 4,935,580, issued to Chao et al., hereby incorporated by reference. Preferred adsorbents for water adsorption include zeolitic molecular sieves such as Zeolite 4A, 5A and 13X and silica gel and activated alumina. Preferred adsorbents for carbon dioxide adsorption include Zeolite 4A, 5A and 13X, although some co-adsorption of hydrocarbons typically occurs on Zeolite 5A and 13X.

It is often desirable when using crystalline molecular sieves that the molecular sieve be agglomerated with a binder in order to ensure that the adsorbent will have suitable physical properties. Although there are a variety of synthetic and naturally occurring binder materials available such as metal oxides, clays, silicas, aluminas, silica-aluminas, silica-zirconias, silica-thorias, silica-berylias, silica-titanias, silica-alumina-thorias, silica-alumina to zirconias, mixtures of these and the like, clay-type binders are preferred. Examples of clays which may be employed to agglomerate the molecular sieve without substantially altering the adsorption properties of the zeolite are attapulgite, kaolin, volclay, sepiolite, polygorskite, kaolinite, bentonite, montmorillonite, illite and chlorite. The choice of a suitable binder and methods employed to agglomerate the molecular sieves are generally known to those skilled in the art and need not be further described herein.

In accordance with the present invention, the feedstream is passed to a first adsorption zone containing a solid adsorbent having selectivity for water at a first zone adsorption temperature effective to adsorb water. A first effluent stream, i.e., dried feedstream having a reduced concentration of water relative to the feedstream is withdrawn from the first adsorption zone. At least a portion of the first zone adsorption effluent stream is passed to a second adsorption zone containing a solid adsorbent having selectivity for carbon dioxide at a second zone adsorption temperature effective to adsorb carbon dioxide. A second zone adsorption effluent stream having a reduced concentration of carbon dioxide relative to the first effluent stream is withdrawn from the second adsorption zone.

Once the adsorbents in the adsorption zones are loaded with water and carbon dioxide to a desired extent which can be determined by those skilled in the art, the loaded adsorption zones are regenerated to remove the adsorbed components. It is to be understood that the adsorption zones are operated in a cyclic manner to approximate continuous operation. That is, when one adsorber bed in an adsorption zone is loaded to a desired extent, the feed flow is diverted to another adsorber bed within the particular adsorption zone. Thus, each adsorption zone can have multiple adsorber beds, e.g., two to six, to approximate continuous operation.

Thermal swing adsorption cycles, are required for use in the process of the present invention. Thermal swing adsorption processes are generally known in the art for various types of adsorptive separations. Generally, thermal swing processes utilize the process steps of adsorption at a low temperature, regeneration at an elevated temperature with a hot purge gas and subsequent cooling down to the adsorption temperature. One process for drying gases generally exemplary of thermal swing processes is described in U.S. Pat. No. 4,484,933, issued to Cohen. The patent describes basic thermal swing processing steps coupled with the use of an auxiliary adsorber bed for improving the regeneration step. Thermal swing processes are often used for drying gases and liquids and for purification where trace impurities are to be removed. Often thermal swing processes are employed when the components to be adsorbed are strongly adsorbed on the adsorbent, i.e., water, and thus, heat is required for regeneration.

Accordingly, the temperatures employed are important for purposes of the present invention. In the first adsorption zone, the adsorption temperature is preferably maintained in a range of from about 32° F., but not lower than the hydrocarbon dew point or the temperature at which formation of hydrates occur, to about 150° F. and more preferably, from about 60° to about 120° F. Since the process of the present invention can readily be used to pretreat feedstreams prior to low temperature hydrocarbon processing, there will often be low temperature streams available that can be used for cooling the feedstream to the desired adsorption temperature. Hence, lower temperatures are especially preferred. By virtue of the present invention, it is possible to maintain the second adsorption zone at a temperature even lower than the first adsorption zone since the water has been removed from the feedstream and thus will not form hydrates in the second adsorption zone. Preferably, the adsorption temperature in the second adsorption zone is from about −40° to 120° F. and, more preferably, from about −20° to 90° F. As noted above with regard to the first adsorption zone, it is undesirable to operate the second adsorption zone at a temperature below the hydrocarbon dew point or hydrate formation point. The lower end of the preferred temperature range in the second adsorption zone generally reflects physical limitations of carbon steel which is generally used in fabrication of the adsorber vessels.

Since thermal swing cycles are employed, the regeneration temperatures must be higher than the adsorption temperatures in order to effect the desorption of the adsorbed components. The preferred temperature ranges for regeneration of the first and second adsorption zones are as follows. In the first adsorption zone, the preferred regeneration temperature is from about 400° to 650° F. and, more preferably, from about 450° to 550° F. In the second adsorption zone, the preferred regeneration temperature is at least about 250° F., preferably from about 300° to 550° F. and, more preferably, from about 350° to 500° F. It is further preferred that the regeneration temperature in the second zone be lower than the regeneration temperature in the first zone. As such, thermal effects which can adversely affect the adsorbents over time, i.e., a reduction in useful life, can be reduced in the second adsorption zone, while water can be effectively desorbed from the first adsorption zone by employing higher regeneration temperatures.

The material used as the purge gas for regenerating the first and second adsorption zones can be obtained from a stream within the processes of the present invention, or alternatively, the source can be from outside the processes of the present invention. When the feedstream contains a light gas such as nitrogen, helium, argon, oxygen, hydrogen or mixtures thereof, the light gas can be used as the purge gas. In a nitrogen rejection unit, for example, a nitrogen-containing stream is withdrawn from a distillation column in the nitrogen rejection unit. This nitrogen-containing stream can conveniently be used as the purge gas in one or both of the adsorption zones and is particularly useful when it is desired to permanently remove the adsorbed components from the feedstream as is often the case when hydrogen sulfide is present in the feedstream. On the other hand, it is often permissible to combine the desorbed components back into the feedstream after the low temperature hydrocarbon processing step has been performed, e.g., when water and carbon dioxide are present. In such a case, the hydrocarbon product stream from the low temperature processing step, or a portion thereof, can be used as the purge gas for the first or second adsorption zones or preferably both, and the desorption effluent streams containing the desorbed components can then be recombined with the product stream, e.g., the hydrocarbon stream from a nitrogen rejection unit. Even more preferably, the adsorption zones are regenerated in series so that the desorption effluent from the carbon dioxide zone, i.e., second adsorption zone, is used as the purge gas for the water zone, i.e., first adsorption zone, and the desorption effluent therefrom is combined with the product gas. Thus, the hydrocarbon product recovery can be substantially higher than for a process which employs pressure swing regeneration in the carbon dioxide adsorption zone.

The amount of purge gas required to regenerate the first and second adsorption zones depends on various factors known to those skilled in the art such as the pressure of the system. Generally, at higher system pressures, more purge gas is required. Typically, however, when the hydrocarbon product gas is used as the purge gas for regenerating one or preferably both of the adsorption zones, typically about 1 to 2% by volume to about 10% by volume of the hydrocarbon product gas is required for regeneration. However, substantial proportions of the product gas, 50% or more can be used if desired. The amount of purge gas required for regeneration can easily be determined by one skilled in the art and need not be further discussed herein.

The pressures used during the adsorption and regeneration steps are generally not critical to the processes of the present invention. Typically, the adsorption steps will be conducted at about the feedstream pressure. The regeneration steps may be conducted at about the adsorption pressure or at a reduced pressure. When a portion of the adsorption effluent is used as a purge gas, it is preferred in one aspect of the invention that the regeneration be conducted at about the adsorption pressure, especially when the desorption effluent stream is re-introduced into a natural gas pipeline, for example. On the other hand, it is often desirable to perform downstream processing steps, e.g., liquefaction, at reduced temperatures and pressures. Thus, the water and carbon dioxide removal steps of the present invention can be employed to facilitate temperature reduction by providing a process stream substantially free of hydrates. The temperature and pressure reduction is preferably conducted by expansion of the adsorption effluent, such as through a valve or turbine, prior to the downstream processing. When at least a portion of a stream from a downstream processing step is used as a purge gas, it is preferred in another aspect of the invention that the regeneration be conducted at a reduced pressure. However, it is important to note that although the pressure reduction will often assist in the regeneration of the adsorber beds, the regeneration is primarily conducted thermally. That is, preferably at least about 50%, more preferably 75% of the adsorbed components are desorbed by the thermal regeneration. It is undesirable in accordance with the present invention to permit the regeneration pressure to fall below 50 psia because the desorption effluent thereby obtained must be compressed substantially in order to be re-introduced into a natural gas pipeline, for example. Preferably, the regeneration pressure will be from about 50 to 1500 psia and more preferably from about 150 to 1000 psia. Even more preferably, the regeneration pressure in the second adsorption zone will be higher than the regeneration pressure in the first adsorption zone.

The cycle time used in the adsorption zones of the process of the present invention is not critical. Typical cycle times in the first adsorption zone can range from about 4 hours to about 1 week or more. In the second adsorption zone where carbon dioxide is adsorbed, typical cycle times range from about 30 minutes to about 8 hours. The determination of the appropriate cycle time for both the first and second adsorption zones can be made by one skilled in the art and need not be further discussed herein. However, it is important to note that by employing separate adsorption zones, it is possible to run longer cycles in the water dehydration zone. Longer cycle times permit more efficient use of the adsorbent because more water can be adsorbed per pound of adsorbent per cycle. In addition, longer cycle times can extend the useful life of the adsorbent.

The present invention is particularly useful when it is desired to remove water and carbon dioxide from hydrocarbon streams prior to low temperature hydrocarbon processing. Typical low temperature hydrocarbon processing operations include nitrogen rejection, helium recovery, liquified natural gas processing and deep ethane recovery. The details of the particular low temperature processing operation do not form a critical aspect of the present invention. However, since the processes of the present invention are especially useful in pretreating nitrogen-containing feeds prior to entering a nitrogen rejection unit, a brief description of a typical nitrogen rejection unit is hereinafter provided.

Generally, a nitrogen rejection unit comprises one or two distillation columns and related condensers, reboilers and heat exchange equipment. A typical single column arrangement for separating nitrogen from a natural gas feedstream comprises a distillation column and a closed loop heat pump, e.g., with methane refrigerant, which reboils and refluxes the column. One or more intermediate reflux condensers are provided and are cooled by both the heat pump and the overhead nitrogen stream from the column. Mixed cryogenic refrigerants can be used in the heat pump as an alternative to the methane heat pump medium. Typical operating pressures are above 300 psia and typical operating temperatures are below 100° F. Further information regarding nitrogen rejection units can be found in previously cited U.S. Pat. Nos. 4,504,295 and 4,662,919 hereby incorporated by reference. Often, when the nitrogen rejection unit comprises two distillation columns, the first distillation column is used to separate methane from liquid natural gas hydrocarbons, i.e., ethane and heavier hydrocarbons. The methane-containing overhead from the distillation column is then passed to the nitrogen rejection distillation column wherein nitrogen and other light gases are separated from the methane.

The present invention is particularly useful in "peak-shaver plants", a common name for natural gas utility plants which process a slipstream of pipeline gas during periods of low natural gas demand in order to liquify and store the gas for subsequent re-introduction into the pipeline during peak demands. The present invention can thus be used to remove water and carbon dioxide from the feedstream prior to liquefaction. During the liquefaction process, a flash gas stream is produced which typically comprises about 30 to 40% of the feedstream. The flash gas is used as a purge gas to regenerate the adsorber beds and produce a desorption effluent stream which is recompressed and re-introduced into the pipeline.

A number of processing advantages that are not possible when both carbon dioxide and water are adsorbed in the same adsorption zone can be achieved by virtue of the present invention. For instance, by providing separate adsorption zones for the $CO_2$ and water adsorption, it is possible to operate the carbon dioxide adsorption zone at a lower temperature than the water dehydration zone. Since adsorption equilibrium generally favors adsorption at lower temperatures, significant increases in carbon dioxide adsorption capacity can be obtained by reducing the adsorption temperature. Such low temperature carbon dioxide adsorption is not possible when water and carbon dioxide are removed in the same adsorption zone since this would result in hydrate formation. As a result of the increased carbon dioxide adsorption capacity, it is often not required to provide a bulk carbon dioxide removal step such as an aqueous amine unit prior to the dehydration step. As far as the adsorption equilibrium is concerned, there is no limit on cooling the dehydrated feedstream prior to carbon dioxide adsorption. Practically, however, as noted above, the low temperature limit is determined by the physical limitations of the adsorption vessel, or otherwise by the feedstream itself, since it is generally not desired to operate below the dew point of the hydrocarbons in the feedstream. When temperatures below the hydrocarbon dew point are employed, it is generally necessary to provide means to separate out the condensed hydrocarbons and route them directly to a hydrocarbon recovery stage, for example. Moreover, cooling the dehydrated feed prior to carbon dioxide adsorption is typically neither difficult nor costly since there are, in addition to cooling water and air, generally numerous low temperature streams available within the low temperature hydrocarbon process such as from a nitrogen rejection unit which could provide a source for indirect heat exchange with the feedstream to obtain the desired temperature.

Another important advantage of separating the adsorption zones is that the present invention allows a portion of the dehydrated carbon dioxide laden gas to be by-passed around the carbon dioxide adsorption zone. In nitrogen rejection units, for example, a typical feed gas specification of less than 250 ppmv (typically about 50 to 150 ppmv) carbon dioxide is required to prevent equipment freeze-up due to carbon dioxide solidification. Since adsorbents such as described herein can easily reduce the carbon dioxide content to much lower levels, e.g., less than 10 ppm, the feed gas specification can be met while allowing a partial by-pass around the adsorption zone. By processing less gas, a reduction in the size of the carbon dioxide adsorption zone can be achieved. In contrast, in a typical combined adsorption bed, such by-passing is not possible since substantially all of the water must be removed prior to the low temperature processing.

Still another advantage that can be achieved by the separation of the adsorption zone is that more efficient regeneration of each of the adsorption zones is possible. It is known that oxygen in the presence of hydrocarbons can react at high temperatures to form carbon oxides and water. See above cited U.S. Pat. No. 4,025,321. It is also known that because water is strongly adsorbed it is generally desirable to maintain a low residual water level on adsorbents used in carbon dioxide removal to avoid competing adsorption between the two species. The present invention provides a solution to this problem by providing for the regeneration of the carbon dioxide adsorption zone when oxygen is present in the purge gas by performing the regeneration at a temperature below that at which the reactions can occur. Moreover, by separating the adsorption zones, the regeneration temperatures can be tailored to provide enhanced performance in both zones. As noted above, a lower temperature regeneration of the carbon dioxide adsorption zone can ensure that the product will meet carbon dioxide specifications by avoiding the water forming reactions. In addition, a higher regeneration temperature in the dehydration zone which is not possible in standard designs due to the above described reactions can provide better stripping of the more strongly adsorbed water to thus achieve enhanced water adsorption capacity. Accordingly, as noted above, it is preferred in the practice of the present invention that the regeneration temperature in the water dehydration zone is higher than the regeneration temperature in the carbon dioxide adsorption zone.

The process of the present invention is hereinafter described with reference to the drawing, FIG. 1. It is to be understood that no limitation to the scope of the claims which follow is intended by the following description. Those skilled in the art will recognize that the process flow diagram has been simplified by the elimination of many necessary pieces of process equipment including valves, heat exchangers, process control systems, pumps, fractionation column overhead and reboiler systems, etc. It may also be readily discerned that the process flows presented in the drawing may be modified in many aspects without departing from the basic overall concept of the invention. For example, the number of heat exchangers shown in the drawings has been held to a minimum for purposes of simplicity. Those skilled in the art will recognize that the choice of heat exchange methods employed to obtain the necessary heating and cooling at various points within the processes and subject to discretion and engineering judgement. Accordingly, there exists many possibilities for indirect heat exchange between different process streams. Depending on the specific location and circumstance of the installation of the subject process, it may also be desired to employ heat exchange against steam, hot oil, refrigerants, or process streams from other processing units not shown on the drawings.

Figure 1:
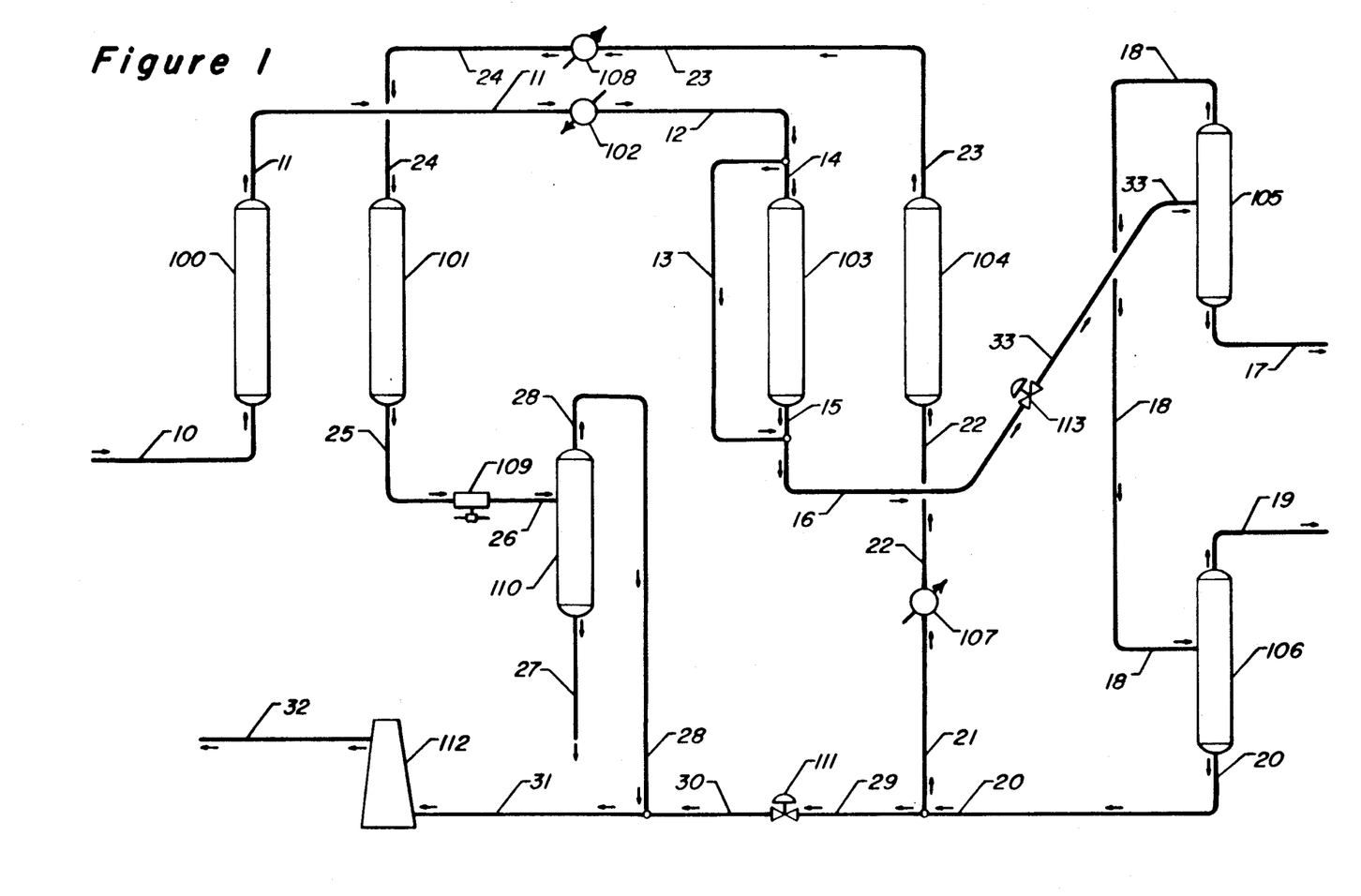
FIG. 1 illustrates a process flow schematic of a low temperature hydrocarbon process for removing water and carbon dioxide in accordance with the present invention.

FIG. 1 illustrates a process flow diagram wherein a first and a second adsorption zone are used to remove water and carbon dioxide from a natural gas feedstream prior to passing the feedstream to a nitrogen rejection unit for separation of the natural gas from the nitrogen. A feedstream containing about 15 vol. % nitrogen, 0.025 vol. % carbon dioxide, 2280 ppmv water, 70 vol. % methane and the balance $C_2+$ hydrocarbons is passed by line 10 to a first adsorption zone, i.e., dehydration zone, which contains adsorber beds 100 and 101, said adsorber beds containing a sufficient quantity of type 4A zeolitic molecular sieve to remove the water from the feedstream. It is to be understood that although only two adsorber beds are shown in the first adsorption zone, any number of adsorber beds can be employed depending upon the desired operation. Preferably, from 2 to about 6 adsorber beds are used in the first adsorption zone. The temperature in adsorber bed 100 during the adsorption step is maintained at a temperature of about 110° F. The pressure of the feedstream is about 650 psia. If necessary, the feedstream can be subjected to heat exchange (not shown) in order to achieve the desired adsorption temperature.

A first zone adsorption effluent stream, i.e., dehydrated feedstream containing less than about 0.1 ppmv water, is withdrawn from adsorber bed 100 by line 11 and cooled in heat exchanger 102 to a temperature of about 40° F. The cooled feedstream is then withdrawn from heat exchanger 102 by line 12 and a portion thereof is passed by line 14 to the second adsorption zone which contains adsorber beds 103 and 104. These adsorber beds contain a sufficient quantity of type 4A zeolitic molecular sieve to absorb the carbon dioxide in line 14. As noted above, with respect to the adsorber beds in the first adsorption zone, any number of adsorber beds can be used in the second adsorption zone. Preferably, however, from 2 to about 6 adsorber beds are used. The remaining portion of the cooled feedstream, line 13, is diverted around adsorber bed 103 in a proportion sufficient to maintain a carbon dioxide concentration of about 50 ppmv in line 16. Adsorber bed 103 is maintained at a temperature of about 40° F. and a pressure of about 640 psia during the adsorption step.

A second zone adsorption effluent stream, i.e., purified feedstream is withdrawn from adsorber bed 103 by line 15, combined with the diverted portion of the cooled feedstream from line 13 and passed by line 16 to an expansion valve 113 wherein the second adsorption effluent stream is expanded and cooled, i.e., by Joule-Thomson cooling, prior to being passed by line 33 to a demethanizer distillation column 105. Such expansion and cooling techniques are known to those skilled in the art and need not be further discussed herein. A bottoms stream containing liquified natural gas hydrocarbons in the $C_2+$ carbon range is withdrawn by line 17 and removed from the process. An overhead stream comprising methane is withdrawn from demethanizer column 105 by line 18 and passed to nitrogen rejection unit 106. The operating conditions in demethanizer column 105 and nitrogen rejection unit 106 are known to those skilled in the art and need not be further disclosed herein. An overhead stream comprising nitrogen is withdrawn from line 19 and removed from the process. However, it is important to note that at least a portion of overhead stream 19 from nitrogen rejection unit 106 can be used to regenerate adsorber 104 as described below with respect to raw product gas stream 20. A raw product gas stream comprising methane, and preferably rich in methane is withdrawn from the nitrogen rejection unit by line 20. More preferably, the raw product gas stream comprises at least 90 vol. % methane.

A portion of the raw product gas stream, i.e., about 5 to 10% is diverted from line 20 and passed by line 21 as a purge gas to heater 107 wherein it is heated to a second zone regeneration temperature of about 450° F. If the feedstream contained oxygen, the regeneration would be conducted at about 350° F. The heated purge gas is passed by line 22 to adsorber bed 104 which is undergoing regeneration at a pressure of about 215 psia. A second zone desorption effluent stream comprising methane, and carbon dioxide is withdrawn from adsorber bed 104 by line 23 and passed to heater 108 wherein it is heated to the first zone regeneration temperature of about 550° F. The heated desorption effluent is then passed by line 24 to adsorber bed 101 which is undergoing regeneration at a pressure of about 210 psia. A first zone desorption effluent stream comprising methane, carbon dioxide and water is withdrawn by line 25 and passed to cooler 109 wherein it is cooled to a temperature of about 119° F. and passed by line 26 to separation vessel 110 wherein an aqueous condensate portion is separated and removed by line 27. An overhead stream depleted in water is withdrawn by line 28 and combined with line 30 as hereinafter described. The undiverted portion of the raw product gas is passed by line 29 through pressure reduction valve 111 wherein the pressure is reduced sufficiently to allow lines 28 and 30 to be combined. A combined product gas stream is then passed by line 31 to compressor 112 wherein it is compressed to a product pressure of about 400 psia and withdrawn from the process by line 32. The recovery of methane from the feedstream is about 98% or more.

The process described above with reference to FIG. 1 is illustrative and is in no way intended to be a limitation on the scope of the claims which follow. In fact, there are many variations which can be made even to the very specific flow scheme shown in FIG. 1. For example, the purge gas stream in line 22 can be divided into two streams so that adsorber beds 101 and 104 can be purged in a parallel relationship rather than in series. Also, in many instances, it may be desirable to eliminate cooler 109 and separation vessel 110 and pass the desorption effluent stream in line 25 directly to the product gas line to be combined with line 30. It also may be desirable to remove compressor 112 and pressure valve 111 from the product gas line and instead utilize a smaller compressor only on the desorption effluent line, e.g., line 25 or 28.

We claim:

1. A process for separating water and carbon dioxide from a feedstream comprising hydrocarbons, water and carbon dioxide, said process comprising the steps of:
   (a) passing the feedstream to a first adsorption zone containing a solid adsorbent having selectivity for water at a first zone adsorption temperature effective to adsorb water and a first zone adsorption pressure and withdrawing a first zone adsorption effluent stream having a reduced concentration of water relative to the feedstream;
   (b) passing at least a portion of the first zone adsorption effluent stream to a second adsorption zone containing a solid adsorbent having selectivity for carbon dioxide at a second zone adsorption temperature effective to adsorb carbon dioxide and a second zone adsorption pressure, said second zone adsorption temperature being lower than said first zone adsorption temperature, and withdrawing a second zone adsorption effluent stream having a reduced concentration of carbon dioxide relative to the first effluent stream;
   (c) passing a first purge gas through the first adsorption zone at a first zone regeneration temperature effective to desorb water from the first adsorption zone and a first zone regeneration pressure and withdrawing a first zone desorption effluent stream comprising water; and
   (d) passing a second purge gas through the second adsorption zone at a second zone regeneration temperature of at least 250° F. and effective to desorb carbon dioxide from the second adsorption zone and a second zone regeneration pressure, said second zone regeneration pressure being not lower than about 50 psia, and withdrawing a second zone desorption effluent stream comprising carbon dioxide.

2. The process of claim 1 wherein the first zone regeneration temperature is higher than the second zone regeneration temperature.

3. The process of claim 1 wherein the feedstream comprises methane and at least one other hydrocarbon selected from ethane, propane and butane.

4. The process of claim 3 further comprising separating the second zone adsorption effluent into a first fraction comprising methane and a second fraction rich in said at least one other hydrocarbon.

5. The process of claim 4 further comprising reducing the temperature and pressure of the second zone adsorption effluent by expansion prior to separating said second zone adsorption effluent to provide an expanded adsorption effluent substantially free of hydrates.

6. The process of claim 4 wherein either one or both of the first purge gas and the second purge gas comprise at least a portion of the first fraction.

7. The process of claim 4 further comprising passing a first portion of the first fraction to the second adsorption zone to comprise at least a portion of the second purge gas and passing at least a portion of the second zone desorption effluent to the first adsorption zone to comprise at least a portion of the first purge gas.

8. The process of claim 7 further comprising combining at least a portion of the first zone desorption effluent with a second portion of the first fraction to provide a combined product gas stream comprising methane.

9. The process of claim 4 wherein the feedstream further comprises at least one light gas selected from nitrogen, helium, argon, oxygen and hydrogen.

10. The process of claim 4 wherein the first fraction comprises said at least one light gas.

11. The process of claim 10 further comprising separating the first fraction into a rejection stream comprising said at least one light gas and a raw product gas stream comprising methane.

12. The process of claim 11 comprising diverting a portion of the raw product gas to the second adsorption zone to comprise at least a portion of the second purge gas and passing at least a portion of the second zone desorption effluent to the first adsorption zone to comprise at least a portion of the first purge gas.

13. The process of claim 12 comprising cooling the first zone desorption effluent to a temperature sufficient to condense water therefrom and combining the water-depleted effluent with the undiverted portion of the raw product gas to provide a combined product stream.

14. The process of claim 1 wherein the first zone adsorption temperature is from about 30° to 150° F.

15. The process of claim 1 wherein the second zone adsorption temperature is from about −40° to 120° F.

16. The process of claim 1 wherein the first zone regeneration temperature is from about 400° to 650° F.

17. The process of claim 1 wherein the second zone regeneration temperature is from about 300° to 550° F.

18. The process of claim 1 wherein the first zone adsorption pressure is from about 100 to 1700 psia and the first zone regeneration pressure is from about 50 to 1500 psia.

19. The pressure of claim 1 wherein the second zone adsorption pressure is from about 100 to 1700 psia and the second zone regeneration pressure is from about 50 to 1500 psia.

20. The process of claim 1 further comprising diverting a portion of the first zone adsorption effluent around the second adsorption zone and combining the diverted portion with the second zone adsorption effluent to provide a combined adsorption effluent.

21. The process of claim 20 wherein said portion is sufficient to provide a concentration of from about 1 to 250 ppmv of carbon dioxide in the combined adsorption effluent.

22. A process for separating water and carbon dioxide from a natural gas feedstream comprising said water, said carbon dioxide, methane, at least one other hydrocarbon selected from ethane, propane, butanes, pentanes and hexanes, and at least one light gas selected from nitrogen, helium, argon, oxygen and hydrogen, said process comprising:
   (a) passing the feedstream to a first adsorption zone containing a solid adsorbent having selectivity for water at a first zone adsorption temperature effective to adsorb water and a first zone adsorption pressure and withdrawing a first zone adsorption effluent stream having a reduced concentration of water relative to the feedstream;
   (b) passing at least a portion of the first zone adsorption effluent stream to a second adsorption zone containing a solid adsorbent having selectivity for carbon dioxide at a second zone adsorption temperature effective to absorb carbon dioxide and a second zone adsorption pressure, said second zone adsorption temperature being lower than said first zone adsorption temperature, and withdrawing a second zone adsorption effluent stream having a reduced concentration of carbon dioxide relative to the first effluent stream;

(c) separating at least a portion of the second effluent stream into a raw product gas stream comprising methane and a rejection stream comprising said at least one light gas;

(d) passing a first purge gas comprising a portion of the raw product gas to the first adsorption zone at a first zone regeneration temperature effective to desorb water from the first adsorption zone and a first zone regeneration pressure and withdrawing a first zone desorption effluent stream comprising water;

(e) passing a second purge gas comprising a portion of the raw product gas to the second adsorption zone at a second zone regeneration temperature of at least 250° F. and effective to desorb carbon dioxide from the second adsorption zone and a second zone regeneration pressure, said second zone regeneration pressure being not lower than about 50 psia, and withdrawing a second zone desorption effluent stream comprising carbon dioxide; and (f) combining the first zone desorption effluent with the remaining portion of the raw product gas to provide a combined product gas rich in methane.

23. The process of claim 22 wherein the first purge gas comprises the second zone desorption effluent stream.

24. The process of claim 23 comprising heating the second purge gas to the second zone regeneration temperature prior to said passing to the second adsorption zone and further heating the second zone desorption effluent stream to the first zone regeneration temperature prior to said passing to the first adsorption zone, said first zone regeneration temperature being higher than said second zone regeneration temperature.

25. The process of claim 22 comprising cooling the first zone adsorption effluent prior to said passing to the second adsorption zone.

26. The process of claim 22 wherein the second zone adsorption effluent is separated in a first distillation column to provide a demethanizer overhead stream comprising methane and a demethanizer bottoms stream comprising said at least one other hydrocarbon and the demethanized overhead stream is separated in a second distillation column to provide the rejection stream and the raw product gas.

* * * * *